(12) United States Patent
Shorey et al.

(10) Patent No.: US 7,579,833 B2
(45) Date of Patent: Aug. 25, 2009

(54) WATER MAPPING USING SURFACE NMR

(75) Inventors: David S. Shorey, Calgary (CA); Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 158 days.

(21) Appl. No.: 11/750,586

(22) Filed: May 18, 2007

(65) Prior Publication Data
US 2008/0284426 A1 Nov. 20, 2008

(51) Int. Cl.
*G01V 3/00* (2006.01)
(52) U.S. Cl. ...................... 324/303; 324/300
(58) Field of Classification Search ............... 324/303, 324/300; 166/245, 303, 50, 273; 422/67
See application file for complete search history.

(56) References Cited

U.S. PATENT DOCUMENTS

| | | | | |
|---|---|---|---|---|
| 5,626,193 A | * | 5/1997 | Nzekwu et al. | 166/303 |
| 5,899,274 A | * | 5/1999 | Frauenfeld et al. | 166/401 |
| 6,923,257 B2 | * | 8/2005 | Wellington et al. | 166/245 |
| 7,121,342 B2 | * | 10/2006 | Vinegar et al. | 166/302 |
| 7,147,057 B2 | * | 12/2006 | Steele et al. | 166/303 |
| 7,156,172 B2 | * | 1/2007 | Becker et al. | 166/288 |
| 7,219,724 B2 | * | 5/2007 | Theriot, Sr. | 166/66.5 |
| 7,367,399 B2 | * | 5/2008 | Steele et al. | 166/303 |
| 7,425,307 B2 | * | 9/2008 | Sohl et al. | 422/67 |
| 2006/0024840 A1 | * | 2/2006 | Conquorgood et al. | 436/178 |

OTHER PUBLICATIONS

Legchenko et al Nuclear Magnetic Resonance as a Geophysical Tool for Hydrologists: Journal of Applied Geophysics; 50 (2002) 21-46.*
Anatoly Legchenko, et al. "A review of the basic principles for proton magnetic resonance sounding measurements". Journal of Applied Geophysics. 50 (2002) 3-19.
USGS, [on-line]; [Retrieved on Apr. 2, 2007], Retrieved from the Internet. http://water.usgs.gov/ogw/bgas/mrs/.
Federal Lands Highway Program, [on-line]; [Retrieved on Apr. 2, 2007], Retrieved fro the Internet. http;///www.cflhd.gov.agm/engApplications/SubsurfaceChartacter/615MappingGroundwater . . . .
O.A. Shushakov, et al. "Hydrocarbon Contamination of Aquifers by SNMR Detection". WM'04 Conference, Feb. 29-Mar. 4, 2004, Tucson, AZ.

* cited by examiner

*Primary Examiner*—Brij B Shrivastav
(74) *Attorney, Agent, or Firm*—Cantor Colburn LLP

(57) ABSTRACT

A method for selecting a location of a wellbore includes: using a nuclear magnetic resonance (NMR) instrument deployed on a surface of a production area, determining a location of ground water in the production area; and locating the wellbore according to the location of the ground water. A system and a computer program product are disclosed as well as a method for performing steam assisted gravity recovery.

18 Claims, 4 Drawing Sheets

WATER MAPPING USING SURFACE NMR

BACKGROUND OF THE INVENTION

1. Field of the Invention

The teachings herein relate to characterization of geologic features, and in particular to mapping of groundwater and hydrocarbon depositions using surface deployments of Nuclear Magnetic Resonance (NMR) technology.

2. Description of the Related Art

Geophysical exploration for hydrocarbon deposits commonly involves drilling of wells into the earth's crust. During the drilling process, or after the process, a variety of technologies are deployed within the wellbore to collect data. The data provided offers explorers insight into potential for locating hydrocarbon resources. One example of such technology is that of Nuclear Magnetic Resonance (NMR). Typically, NMR instruments are lowered into a respective wellbore and the data are collected from some depth below the surface. As one might imagine, collecting data in this manner is quite expensive.

Although performing subterranean measurements can provide data not otherwise available, such measurements are not without limitations. For example, performing measurements from within a wellbore provides users with data up to a limited distance away from each wellbore. Accordingly, to obtain accurate depictions of formations for a geographic area, many wells must be drilled. This can be cost prohibitive. Thus, NMR technology has been deployed for surface measurements.

Steam Assisted Gravity Drainage (SAGD) is an enhanced oil recovery technology for heavy crude oil and bitumen. Two parallel horizontal oil wells are drilled in the formation. The upper well is used to inject steam and the lower one is used to collect water that results from the condensation of the injected steam as well as the crude oil or bitumen. The injected steam heats the crude oil or bitumen and lowers its viscosity which allows it to flow down into the lower wellbore. The large density contrast between steam on one side and water/hot heavy crude oil on the other side ensures that steam is not produced at the lower production well. The water and crude oil or bitumen is recovered to the surface by several methods such as natural steam lift where some of the recovered hot water condensate flashes in the riser and lifts the column of fluid to the surface, by gas lift where a gas (usually natural gas) is injected into the riser to lift the column of fluid, or by pumps such as progressive cavity pumps that work well for moving high-viscosity fluids with suspended solids.

The original SAGD wells were drilled horizontally from a tunnel in the limestone underburden, accessed with vertical mineshafts. The concept coincided with development of directional drilling techniques that allowed companies to drill horizontal wells accurately, cheaply and efficiently, to the point that it became hard to justify drilling a conventional vertical well any more. With the low cost of drilling horizontal well pairs, and the very high recovery rates of the SAGD process (up to 60% of the oil in place), SAGD is economically attractive to oil companies. This technology is now being exploited due to increased oil prices. For example, many SAGD projects are in progress in the Canadian oil sands, since this region is home of one of the largest deposits of bitumen in the world.

Ground water present in a production layer should be detected and delineated when planning well trajectories in the SAGD process. It is desirable to reduce a number of wells drilled for the purpose of the detection and delineation.

Accordingly, what are needed are techniques for mapping the ground water. Preferably, the techniques are low cost, rapidly deployable and make use of existing technologies, such as NMR.

BRIEF SUMMARY OF THE INVENTION

Disclosed is a method for selecting a location of a wellbore, that includes: using a nuclear magnetic resonance (NMR) instrument deployed on a surface of a production area, determining a location of ground water in the production area; and locating the wellbore according to the location of the ground water.

Also disclosed is a system for selecting a location of a wellbore, that includes: a surface deployable nuclear magnetic resonance (NMR) instrument including a transmitter, a receiver, and an antenna, the instrument adapted for providing an indication of a location for drilling a wellbore by indication of ground water in a production area.

In addition, a computer program product stored on machine readable media, the product including machine executable instructions for selecting a location of a wellbore, is provided and includes instructions for: receiving data from a nuclear magnetic resonance (NMR) instrument deployed on a surface of a production area; determining a location of ground water in the production area from the data; and locating the wellbore according to the location of the ground water.

Further disclosed is a method for performing steam assisted gravity drainage recovery, that includes using a nuclear magnetic resonance (NMR) instrument deployed on a surface of a production area, determining a location of geologic features in the production area; locating at least one wellbore according to the location; and using the at least one wellbore to supply steam for the recovery.

BRIEF DESCRIPTION OF THE DRAWINGS

Referring now to the drawings wherein like elements are numbered alike in the several Figures.

DETAILED DESCRIPTION OF THE INVENTION

The teachings herein provide for surface deployment of Nuclear Magnetic Resonance (NMR) technology to obtain data regarding geologic formations at depths of up to about 500 meters (m). This technology is particularly useful for detection and delineation of ground water when planning well trajectories in heavy oil development. This technique may be used to provide for reductions to the number of wells drilled during exploration.

Figure 1:
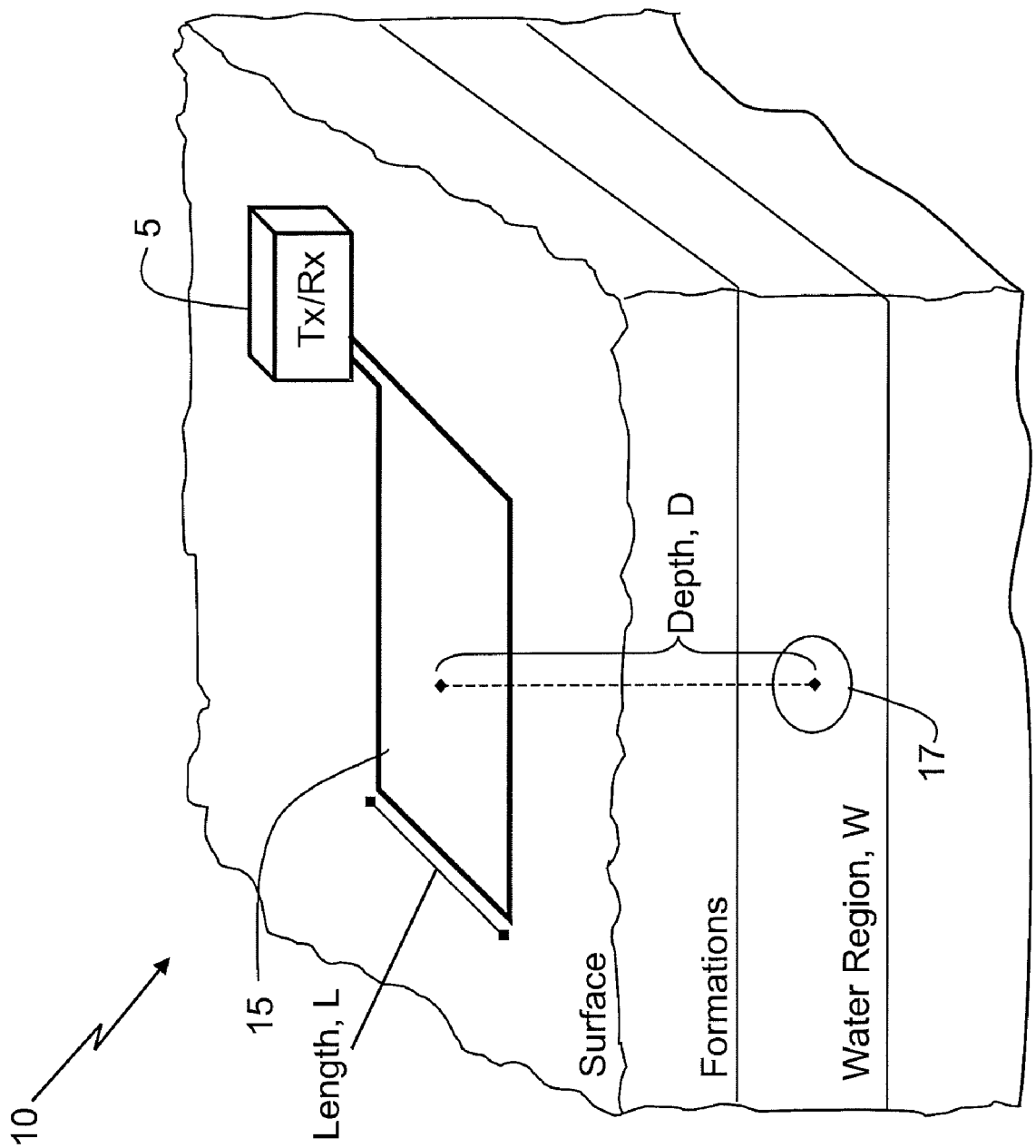
FIG. 1 depicts aspects of a prior art instrument for making NMR surface measurements.

FIG. 1 illustrates an implementation of a prior art NMR surface technique. As shown in FIG. 1, a prior art NMR instrument 10 includes a single loop antenna 15. The single loop antenna 15 has a current loop having a length, L, of about 300 meters (m) along one side. An electronics unit 5 is also included. Typically, the electronics unit 5 includes a transmitter (Tx) and a receiver (Rx). Other electronics as are known in the art may be included with the electronics unit 5 or coupled to the electronics unit 5 (through, for example, some form of a network interface).

The prior art NMR instrument 10 is used to provide a magnetic resonance signal in the earth formations in order to identify a ground water region, W. Shown residing in the water region, W, is a fragment 17 of the ground water region, W.

During operation, in some embodiments, the transmitter, Tx, drives alternating current (AC) at a proton resonance frequency through the single loop antenna 15. The current is driven in a form of an pulse of alternating current (AC). An AC magnetic field generated by the antenna 15 as a result of the pulsed AC current causes precession of nuclear spins for nuclei in a region of interest. The precession of the nuclear spins in the Earth's magnetic field induces an NMR signal in the same antenna 15 and output signal that is processed by the receiver, Rx. This procedure may be repeated to improve signal-to-noise responses by employing statistical analyses. The signal provides information regarding hydrological parameters as a function of depth, D. An NMR signal acquired after a single AC pulse is referred to as a "free induction decay" signal (FID). One or more additional AC pulses can be generated by the transmitter facilitating acquiring one or more spin echoes.

Figure 2:
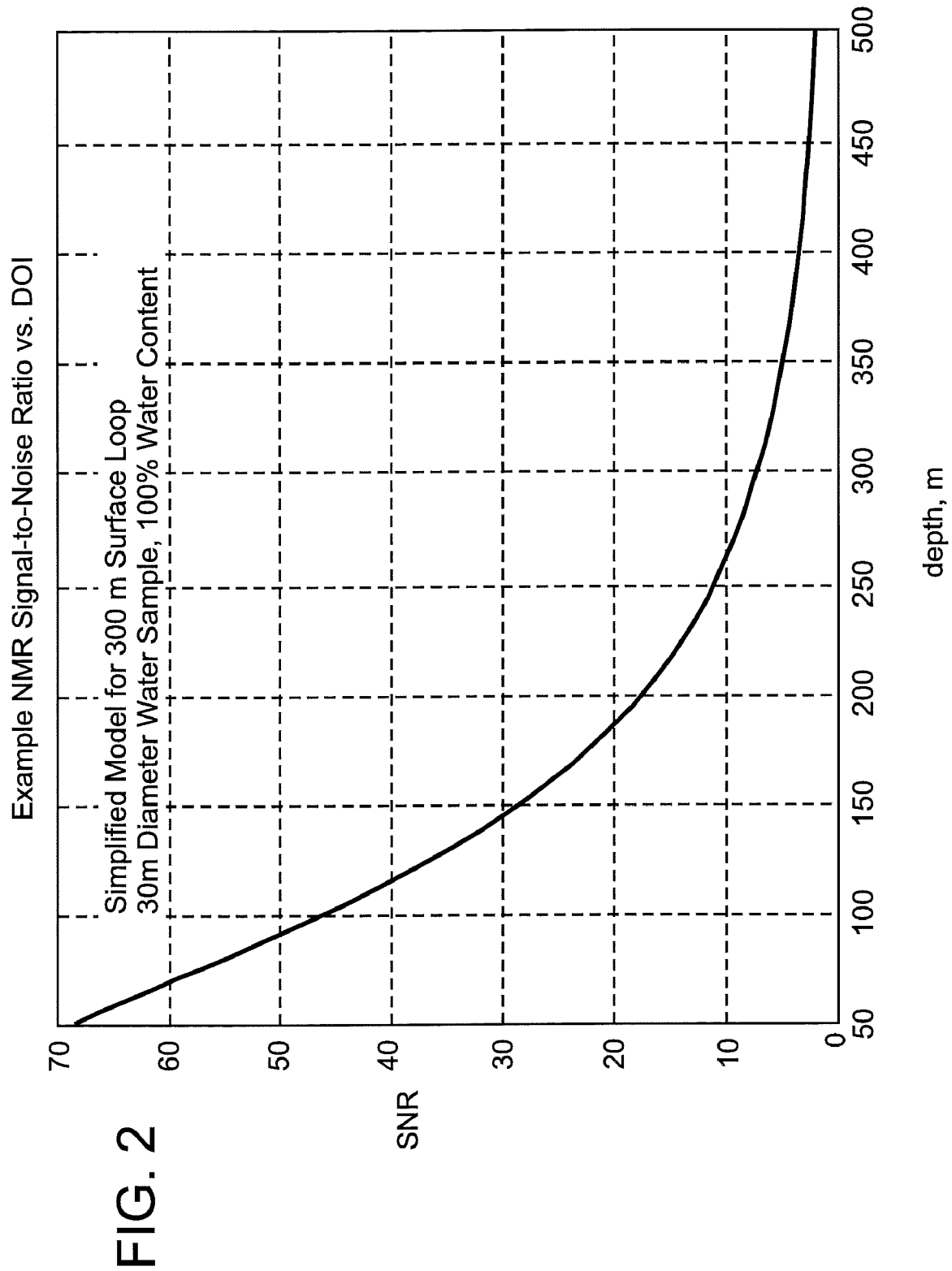
FIG. 2 is a graph representing an exemplary signal-to-noise ratio (SNR) for a thirty meter diameter water region as a function of depth.

FIG. 2 is a graph illustrating a signal-to-noise ratio (SNR) as a function of depth of investigation (DOI) for the prior art NMR instrument 10 of FIG. 1. In FIG. 2, the SNR was modeled for a water region having a thirty (30) meter (m) diameter. The water region was located at different depths, as is shown. FIG. 2 provides an illustration of potential minimum volume detection level and minimum measured time for the instrument 10 of FIG. 1.

Figure 3:
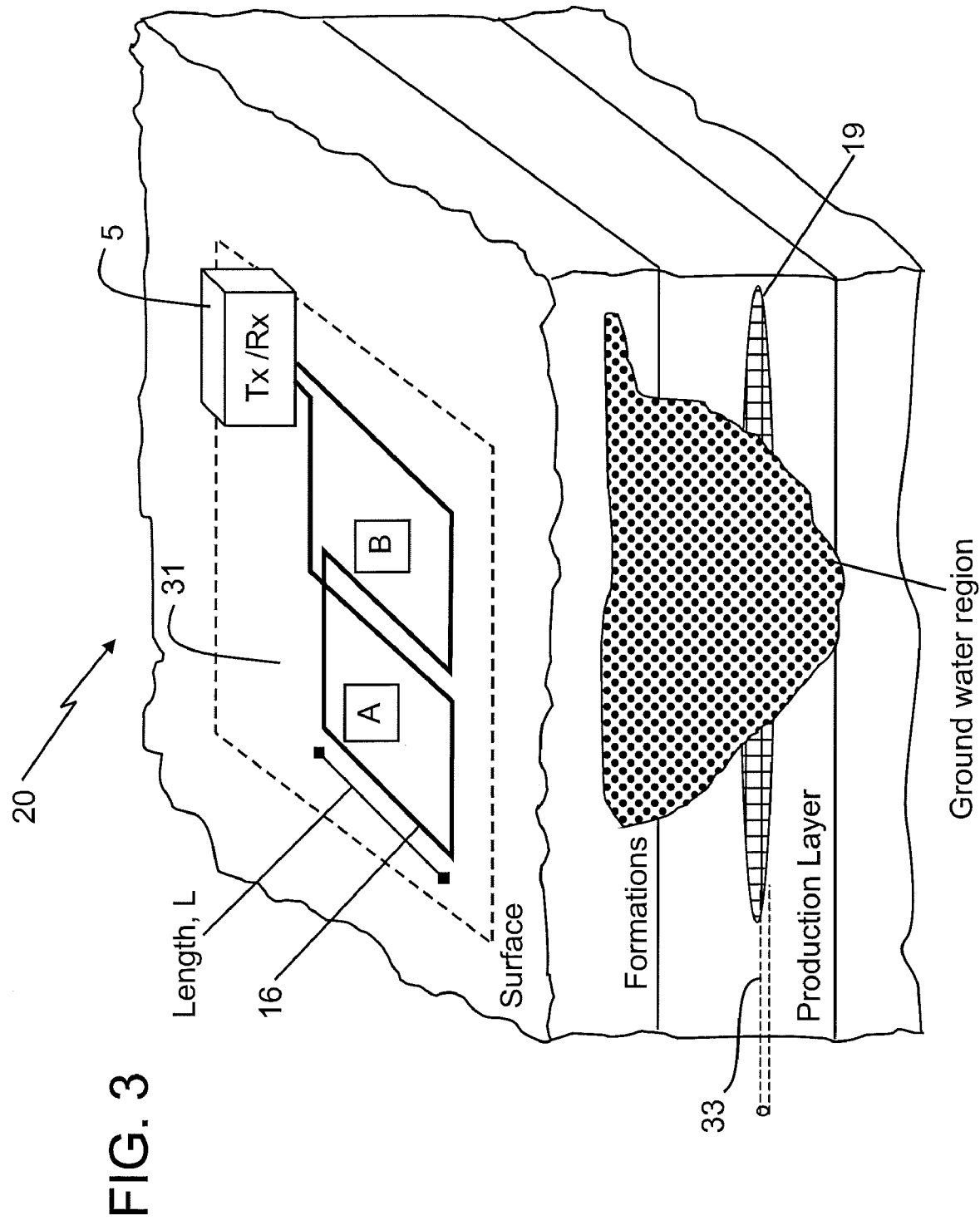
FIG. 3 depicts aspects of a deployment of surface NMR technology disclosed herein.

An embodiment of an improved NMR instrument 20 is presented in FIG. 3. In FIG. 3, a double loop antenna 16 is shown. The double loop antenna 16 is deployed within a production area 31 and implemented as a "butterfly" coil. When used in transmit mode, this type of coil generates a substantial component of the audio-frequency (AF) magnetic field in a plane parallel to the Earth's surface. Accordingly, the butterfly coil provides more effective NMR excitation in places where the Earth's magnetic field vector (northern geographic areas) is substantially in a vertical direction. An important advantage of the "butterfly" loop in receive mode, is an inherent immunity to the environmental noise which typically dominates in the total noise in surface NMR. For example, voltage induced by environmental noise in section A and section B of the double loop antenna 16 will have opposite phases and therefore cancel each other.

An overall size of the "butterfly" loop should be preferably larger that of a single loop embodiment in order to make up for sensitivity reduction as a function of depth.

Also shown in FIG. 3 is a ground water region 18. The ground water region 18 intersects a heavy oil production layer 19. Since both water and oil contain hydrogen, protons are excited in both fluids. However, the NMR signal associated with heavy oil decays much faster than that of the water regions. Therefore, NMR signals associated with water can be easily differentiated from those due to oil. In some embodiments, practical dead time of the NMR measurements in the Earth's magnetic field makes the heavy oil signal invisible in the measurements. Thus, only the water signal is recorded.

By use of surface NMR instruments, operators are better equipped to find and delineate the water region 18 and other features that are useful in planning the Steam Assisted Gravity Drainage (SAGD) process. For example, in the illustration of FIG. 3, use of the improved NMR instrument 20 provides for identification of the ground water region 18 prior to drilling. Accordingly, exploration may be planned to avoid such features and thus provide for economic drilling of wellbores. In particular, the production well pair (horizontal wells) is drilled in such a way that avoid ground water regions 18. One wellbore 33 of the pair of production wellbores is depicted in FIG. 3.

Figure 4:
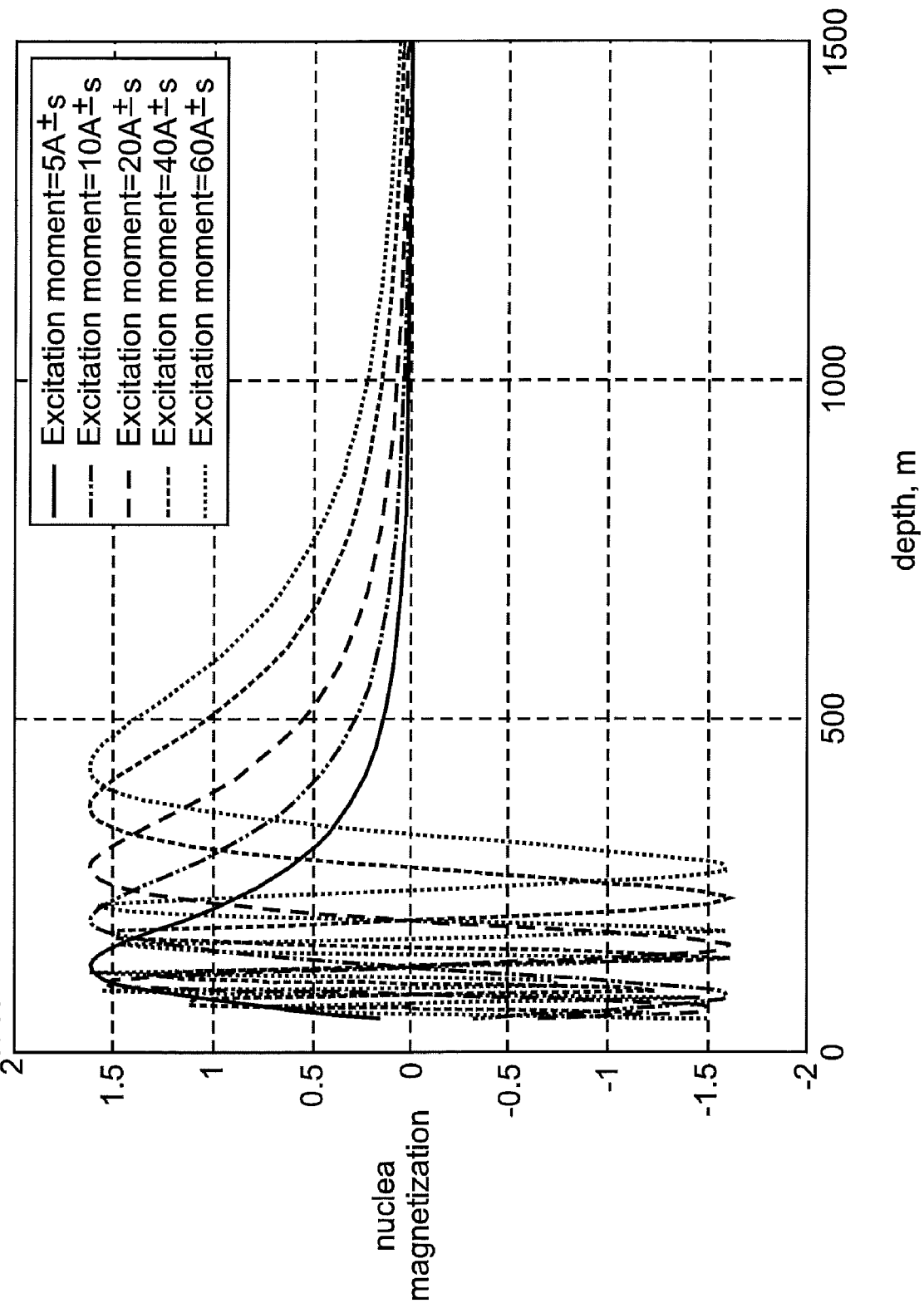
FIG. 4 is a graph representing in-depth selectivity of NMR excitation as a function of depth.

Many techniques, such as those known to those skilled in the art, may be used to obtain data using surface deployments of NMR instruments. For example, one skilled in the art will recognize that NMR excitation properties may be set to reach a peak value (i.e., optimized or maximized) at different depths. Depth selection is typically dependant upon an excitation moment of the current loop. FIG. 4 illustrates the principle of vertical selectivity in surface NMR. The data presented in FIG. 4 are for nuclear magnetization of a free induction decay (FID) after a single audio-frequency (AF) pulse (having a frequency, for example, of about 2 kHz). A better spatial selectivity can be expected when echo signal is acquired after two-pulse excitation.

The teachings herein provide for surface NMR technology that is modified over prior art embodiments to provide for a DOI of up to about 500 m. Further, the teachings herein provide for adjusting measurement techniques for use in northern regions where the Earth's magnetic field is almost vertical to the surface (e.g., in Canada, where a vertical-to-horizontal component ratio is about 5:1).

In particular, the teachings herein call for, among other things: use of narrow frequency bands as water has a long NMR relaxation time, $T_2^*$; longer measurement times (typically in minutes), which provides for substantial data stacking and improved SNR; calibration of the NMR instrument 10 using logging data. In some embodiments, spatial resolution of about 50 meters to about 100 meters is acceptable.

Although surface NMR disclosed herein provides certain advantages, surface induction technology can be implemented in conjunction with NMR. That is, the loop antennae 15, 16 may be used for either or both technologies. In fact, aspects of the electronics 5 may serve the dual purpose as well. One of various ways to combine NMR and induction techniques is to perform induction measurements while waiting for NMR signal recovery (about three to five times the NMR longitudinal relaxation time, $T_1$). The induction measurements may be implemented either in multi-frequency or transient versions. NMR should be preferred to surface electromagnetic (EM) technology (e.g. induction multi-frequency or transient) since resistivity contrast between water regions and heavy oil deposits may be relatively poor.

One skilled in the art will recognize that a variety of embodiments may be had. For example, multiple antenna systems may be operated. Further, multiple loops may be included in any one or more of the antenna. A display may be incorporated into the instrument 20 along with algorithms and other resources. Typically, these other resources are useful for indicating an area for drilling. That is, these resources may account for locations of ground water and provide indications of where to drill in order to avoid the ground water. In some embodiments, these resources make use of other information, such as logging data in addition to NMR measurements with the instrument 20 to provide indications of where to drill each wellbore.

In support of the teachings herein, various analysis components may be used, including digital and/or an analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, power supply (e.g., at least one of a generator, a remote supply and a battery), motive force (such as a translational force, propulsional force or a rotational force), optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for selecting a location of a wellbore, the method comprising:
   using a nuclear magnetic resonance (NMR) instrument deployed on a surface of a production area comprising regions of ground water and heavy oil, determining a location of the ground water in the production area and the heavy oil by differentiating signal decay; and
   locating the wellbore according to the location information.

2. The method as in claim 1, wherein the wellbore is located to avoid the ground water.

3. The method as in claim 1, wherein using comprises applying a pulse of alternating current (AC) having a frequency substantially equal to an NMR frequency in the Earth's magnetic field and receiving a signal from the instrument.

4. The method as in claim 1, wherein determining comprises performing multiple measurements with the instrument.

5. The method as in claim 3, further comprising performing a statistical analysis of measurement data.

6. The method as in claim 1, wherein using comprises performing a measurement at a selected depth.

7. The method as in claim 1, wherein using comprises performing a measurement using narrow frequency bands.

8. The method as in claim 1, wherein determining comprises performing data stacking.

9. The method as in claim 1, further comprising calibrating the NMR instrument to logging data for the production area.

10. The method as in claim 1, wherein the NMR instrument is deployed for canceling out environmental noise.

11. A system for selecting a location of a wellbore, the system comprising:
    a surface deployable nuclear magnetic resonance (NMR) instrument comprising a transmitter, a receiver, and an antenna, the instrument adapted for providing an indication of a location for drilling a wellbore in a production area determined by differentiation of a decay of NMR signals associated with ground water and heavy oil in the production area.

12. The system as in claim 11, wherein the antenna comprises a single loop.

13. The system as in claim 11, wherein the antenna comprises at least a double loop.

14. The system as in claim 11, wherein the instrument is adapted for using audio-frequencies.

15. A computer program product stored on machine readable media, the product comprising machine executable instructions for selecting a location of a wellbore, the instructions comprising instructions for:
    receiving data from a nuclear magnetic resonance (NMR) instrument deployed on a surface of a production area;
    determining a location of ground water from a location of heavy oil in the production area from the data by differentiating signal decay for each of the ground water and the heavy oil; and
    indicating a location for the wellbore according to the differentiating.

16. The product as in claim 15, further comprising instructions for providing a display to a user.

17. The product as in claim 15, comprising instructions for further using well logging data in the determining.

18. A method for performing steam assisted gravity drainage recovery, the method comprising:
    using a nuclear magnetic resonance (NMR) instrument deployed on a surface of a production area, determining a location of ground water and a location of heavy oil in the production area data by differentiating signal decay for each of the ground water and the heavy oil;
    locating at least one wellbore according to location information; and
    using the at least one wellbore to supply steam for the recovery.

* * * * *